US00PP31515P2

(12) United States Plant Patent
Van Swieten

(10) Patent No.: US PP31,515 P2
(45) Date of Patent: Mar. 3, 2020

(54) ***PHALAENOPSIS* ORCHID PLANT NAMED 'PHALGOPEL'**

(50) Latin Name: ***Phalaenopsis* hybrid**
Varietal Denomination: PHALGOPEL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,157

(22) Filed: Feb. 26, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

(56) References Cited

PUBLICATIONS

EU Community Plant Variety Rights Application No. 2018/1178, Application n°A201801081, filed Apr. 26, 2018, 8 pages.
EU Community Plant Variety Office Official Gazette, Mar. 2018, Jun. 15, 2018, cover page and pp. 35, 55.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGOPEL', particularly characterized by having large, white flowers with greenish-white lips, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGOPEL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGOPEL'.

The new *Phalaenopsis* plant is a product of a planned breeding program conducted by the inventor in Bleiswijk, The Netherlands. The objective of this breeding program was to create a new *Phalaenopsis* plant with numerous attractive, large, white flowers with greenish-white lips, suitable for potted plant production.

The new *Phalaenopsis* plant 'PHALGOPEL' is a result of cross-pollination made by the inventor in February 2009 in Bleiswijk, The Netherlands, of the proprietary female, or seed parent, *Phalaenopsis* hybrid '01-1988' (unpatented) with the proprietary male, or pollen parent, *Phalaenopsis* hybrid 'PHALDIPWEQ' (U.S. Plant Pat. No. 26,466).

The new *Phalaenopsis* was selected by the inventor as a single plant within the progeny of the stated cross-pollination in a controlled greenhouse in Bleiswijk, The Netherlands, in May 2012. Asexual reproduction of the new *Phalaenopsis* plant by meristem tissue culture since 2015 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 26, 2018 by Applicant who obtained the subject matter disclosed directly from the Inventor. 'PHALGOPEL' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGOPEL' as a new and distinct variety of *Phalaenopsis* plant:

1) Large, white flowers with greenish-white lips;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week-old plants in December 2018. Colors in the photographs may differ from the color values cited in the detailed botanical description, which accurately describe the actual colors of the new variety.

DESCRIPTION OF THE NEW VARIETY

Figure 1:
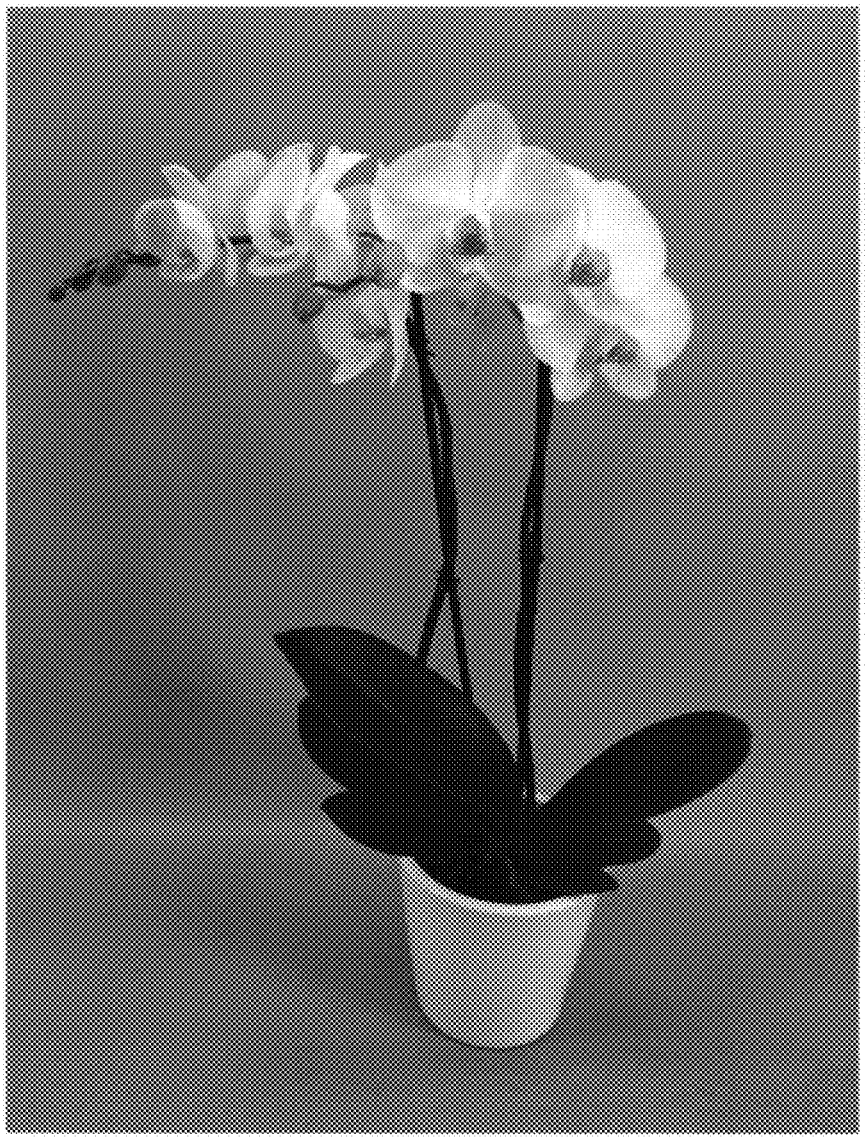
FIG. 1 shows the overall plant habit, including blooms, buds and foliage of 'PHALGOPEL'.
Figure 2:
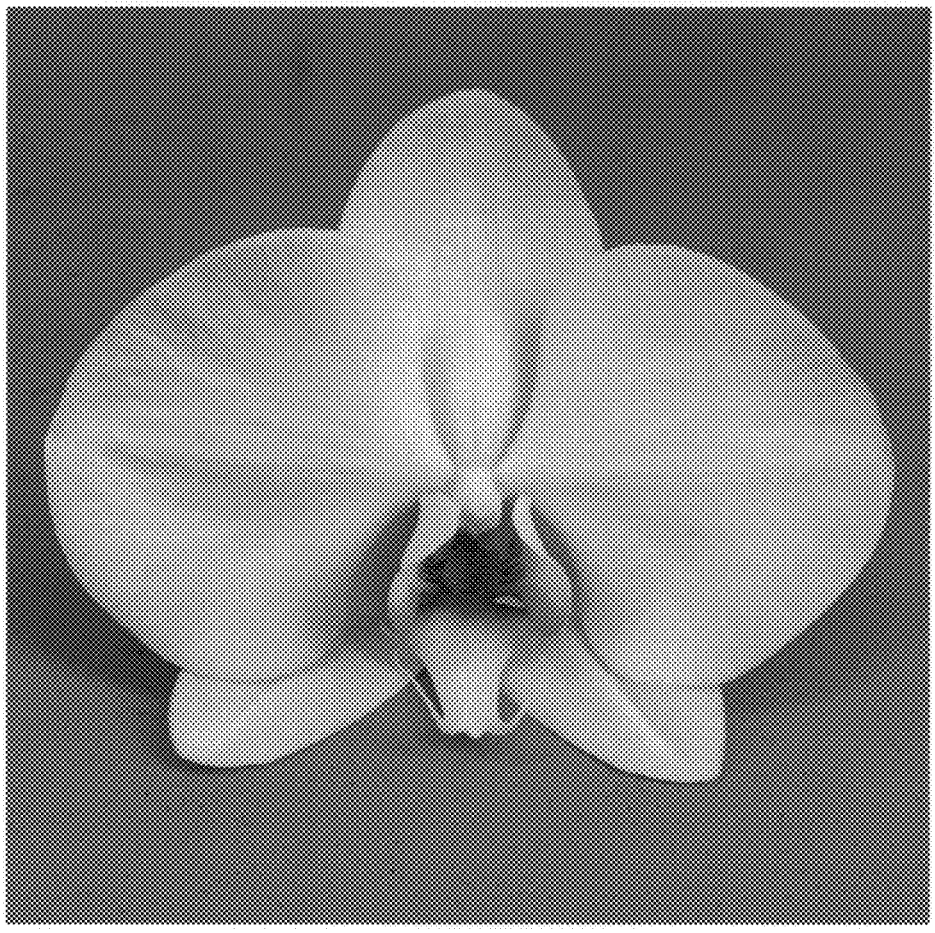
FIG. 2 shows a close-up of a flower of 'PHALGOPEL'.
Figure 3:
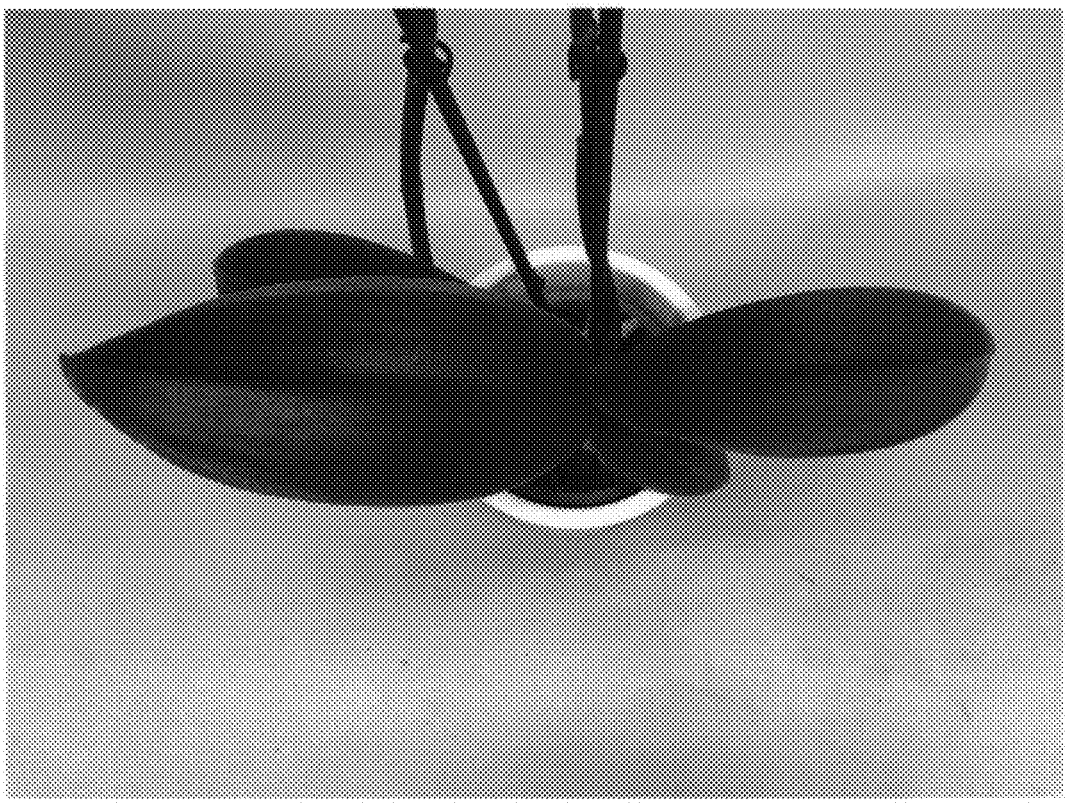
FIG. 3 shows an overhead view of the leaves of 'PHALGOPEL'.

The following detailed description sets forth the distinctive characteristics of 'PHALGOPEL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in December 2018 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALGOPEL'.

Parentage:
- *Female parent*.—*Phalaenopsis* cultivar '01-1988' (unpatented).
- *Male parent*.—*Phalaenopsis* cultivar 'PHALDIPWEQ' (U.S. Plant Pat. No. 26,466).

Propagation:
- *Type*.—Meristem tissue culture.

Roots:
- *Root description*.—Greyed-green (between RHS 190B and 190C) colored roots with branching lateral roots having light yellow-green (RHS 145C) colored root tips.

Plant:
- *Commercial crop time to flowering*.—Following asexual propagation (in-vitro), the rooted cuttings grow for 20-24 weeks. After transplantation into 12-cm pots, the plants are finished after 48 to 50 weeks.
- *Growth habit of peduncle*.—Upright to slightly pendant with raceme inflorescence.
- *Height (from soil level to top of inflorescence)*.—Approximately 52.0 cm to 57.0 cm.
- *Width (measured from leaf tips)*.—About 30.0 cm to 32.0 cm.
- *Vigor*.—Strong.

Leaves:
- *Mature leaves*.—Quantity per plant: 7 to 9 leaves are produced before flowering. Length (fully expanded): 17.0 cm to 23.0 cm. Width: 8.0 cm to 9.0 cm. Shape: Oblong. Base shape: Moderately elongated. Apex: Obtuse unequal. Leaf blade angle with the petiole (measured from the horizontal position): Between 30 degrees and 40 degrees. Leaf margin: Entire. Color: Upper surface: RHS 147A. Lower surface: RHS 146A. Texture (upper surface): Rough. Texture (lower surface): Smooth. Thickness: 2.5 mm to 2.9 mm. Venation: Pattern: Parallel. Color of the midvein: Upper surface: RHS 147A. Lower surface: RHS 146B.

Peduncle:
- *Quantity per plant*.—1 to 2.
- *Number of flowers per peduncle*.—8 to 12.
- *Length*.—52.0 cm to 57.0 cm.
- *Diameter*.—6.5 mm to 7.5 mm.
- *Strength*.—Strong.
- *Aspect*.—Upright to slightly pendant.
- *Texture*.—Smooth.
- *Color*.—Green (RHS 146A).
- *Internode length*.—4.0 cm to 5.0 cm.

Inflorescence description:
- *Appearance*.—Upright to slightly pendant, raceme inflorescence with bilaterally symmetrical flowers that open in succession beginning with the lowermost flower.
- *Inflorescence size*.—Height (from base to tip): 200.0 mm to 250.0 mm. Diameter: 140.0 mm to 160.0 mm.
- *Flowering time*.—First flowers can be expected 10 to 11 months after planting in a 12-cm pot.
- *Flower*.—Height: 95.0 mm to 100.0 mm. Diameter: 110.0 mm to 115.0 mm. Depth of lip: 26.0 mm to 28.0 mm.
- *Flower longevity*.—On the plant: 12 to 18 weeks.
- *Fragrance*.—Absent.
- *Flower bud*.—Average size: Large. Length: 27.0 mm to 29.0 mm. Width: 19.0 mm to 21.0 mm. Shape: Egg shaped. Color: Light yellow-green (RHS 145B) with a touch of purplish-red (RHS N77B).
- *Petals*.—Arrangement: Open/free. Shape: Semi-circular. Apex: Rounded asymmetric. Margin: Slightly undulated. Length (from base to tip): 51.0 mm to 53.0 mm. Width: 62.0 mm to 64.0 mm. Color (when fully opened): Upper surface: Basic color: White (RHS NN155C). Over color: Absent. Lower surface: Basic color: White (RHS NN155C). Over color: Absent.
- *Dorsal sepal*.—Shape: Elliptic. Apex: Obtuse to slightly emarginated. Margin: Entire. Length (from base to tip): 54.0 mm to 56.0 mm. Width: 39.0 mm to 41.0 mm. Color (when fully opened): Upper surface: Basic color: White (RHS NN155C). Over color: Absent. Lower surface: Basic color: White (RHS NN155C). Over color: Slightly light yellow-green (RHS 145D) and slightly light reddish-purple (RHS N78D).
- *Lateral sepals*.—Shape: Ovate. Apex: Obtuse asymmetric. Margin: Entire. Length (from base to tip): 54.0 mm to 56.0 mm. Width: 32.0 mm to 34.0 mm. Color (when fully opened): Upper surface: Basic color: White (RHS NN155C). Over color: Light yellow-green (RHS 145D) at the base. Lower surface: Basic color: White (RHS NN155C). Over color: Light yellow-green (between RHS 145C and 145D) and slightly light reddish-purple (RHS N78D) toward margin.
- *Labellum (lip)*.—Whiskers: Present. Length of whiskers: 27.0 mm to 29.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 22.0 mm to 24.0 mm. Width: 18.0 mm to 20.0 mm. Color: Upper surface: White (RHS NN155C) with dark red stripes (RHS 183B) at the base and greenish-yellow (RHS 151B) on one side. Lower surface: White (RHS NN155C); greenish-yellow (RHS 151C) at the base toward the margin; yellow margin (RHS 15A) on one side.

*Apical lobe*.—Shape: Triangular. Margin: Entire. Length: 23.0 mm to 25.0 mm. Width: 23.0 mm to 25.0 mm. Color: Upper surface: Dark red margin (RHS 183B) at the base; greenish-yellow (mix of RHS 1A and 151B) toward wings; white (RHS NN155C) toward whiskers. Lower surface: White (RHS NN155C) with greenish-yellow wings (RHS 151B) and yellow tips (wing tip) (RHS 15A).

*Callus*.—Average size: Large. Height: 7.0 mm to 8.0 mm. Length: 7.0 mm to 8.0 mm. Width: 5.0 mm to 6.0 mm. Color: Yellow (RHS 15A); dotted (RHS 183B).

Reproductive organs:

*Column*.—Length: 9.0 mm to 11.0 mm. Diameter: 6.3 mm to 6.6 mm. Color: White (RHS NN155C).

*Pollinia*.—Quantity: 2. Diameter: 0.9 mm to 1.1 mm. Color: Orange (RHS 25A).

*Ovary*.—Length: 13.0 mm to 15.0 mm. Diameter: 2.8 mm to 3.3 mm. Color: Light yellow-green (RHS 145C) and light reddish-purple (RHS N78D) toward the flower.

*Pedicel*.—Length: 39.0 mm to 41.0 mm. Diameter: 3.4 mm to 3.9 mm. Color: Yellow-green (RHS 14A) at the base; light yellow-green (between RHS 145B and 145C) and light reddish-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGOPEL' differs from female parent plant '01-1988' (unpatented) in that 'PHALGOPEL' has white whiskers, a moderately elongated leaf base, and a leaf blade angle with the petiole that is 30 to 40 degrees, whereas '01-1988' has yellow whiskers, a very elongated leaf base, and a leaf blade angle with the petiole that is 5 to 15 degrees.

'PHALGOPEL' differs from male parent plant 'PHALDIPWEQ' (U.S. Plant Pat. No. 26,466) in that 'PHALGOPEL' has obtuse unequal leaf apexes, rounded asymmetric petal apexes, and a leaf blade angle with the petiole of 30 to 40 degrees, whereas 'PHALDIPWEQ' has mucronate unequal leaf apexes, mucronate symmetric petal apexes, and a leaf blade angle with the petiole of 10 to 25 degrees.

'PHALGOPEL' is most similar to the commercial *Phalaenopsis* plants named 'PHALFOUDI' (U.S. Plant Pat. No. 29,453) and 'PHALFMACON' (U.S. Plant Pat. No. 29,614). 'PHALGOPEL' differs from the commercial variety 'PHALFOUDI' in that 'PHALGOPEL' has white whiskers, whereas 'PHALFOUDI' has yellow whiskers. Additionally, 'PHALGOPEL' has larger flowers, longer whiskers, longer internodes, and longer dorsal sepals than 'PHALFOUDI'.

'PHALGOPEL' differs from the commercial variety 'PHALFMACON' in that 'PHALGOPEL' has white whiskers, whereas 'PHALFMACON' has yellow whiskers with yellow-orange toward the tip. Additionally, 'PHALGOPEL' has shorter whiskers than 'PHALFMACON'.

I claim:

1. A new and distinct variety of *Phalaenopsis* plant named 'PHALGOPEL', substantially as described and illustrated herein.

* * * * *